United States Patent [19]
Lindberg et al.

[11] Patent Number: 6,143,771
[45] Date of Patent: *Nov. 7, 2000

[54] COMPOUNDS

[75] Inventors: Per Lennart Lindberg, Mölndal; Sverker von Unge, Fjärås, both of Sweden

[73] Assignee: AstraZeneca AB, Sodertalje, Sweden

[*] Notice: This patent is subject to a terminal disclaimer.

[21] Appl. No.: 09/419,456

[22] Filed: Oct. 15, 1999

Related U.S. Application Data

[63] Continuation of application No. 08/899,931, Jul. 24, 1997, abandoned, which is a continuation of application No. 08/376,512, Jan. 23, 1995, Pat. No. 5,714,504, which is a continuation-in-part of application No. 08/256,174, Jun. 28, 1994, Pat. No. 5,693,818.

[30] Foreign Application Priority Data

May 28, 1993 [SE] Sweden ................................... 9301830

[51] Int. Cl.$^7$ .................................................... A61K 31/44
[52] U.S. Cl. ............................................................ 514/338
[58] Field of Search ................................................ 514/338

[56] References Cited

U.S. PATENT DOCUMENTS

| | | | |
|---|---|---|---|
| 4,738,974 | 4/1988 | Brandström | 514/338 |
| 5,714,504 | 2/1998 | Lindberg et al. | 514/338 |
| 5,877,192 | 3/1999 | Lindberg et al. | 514/338 |
| 5,888,535 | 3/1999 | Gray | 424/449 |

FOREIGN PATENT DOCUMENTS

| | | |
|---|---|---|
| 0005129 | 4/1981 | European Pat. Off. |
| 0124495 | 1/1987 | European Pat. Off. |
| 4035455 | 11/1990 | Germany |
| 9501977 | 1/1995 | WIPO |

OTHER PUBLICATIONS

Sverker von Unge et al., Stereochemical assignment of the enantiomers of omeprazole from X–ray fenchyloxymethyl derivative of (+)–(R)–omeprazole, *Tetrahedron: Asymmetry,* vol. 8, No. 12, p. 1997.

Cairns, et al. "Enantioselective HPLC determination . . . " Journal of Chromatography 8, 666 (1995) 323–328.

Yamada et al. "Synthesis and isomerization of optical active . . . " Chem. Pharm. Bull. 42(8) (1994) 1679–1681.

K. Miwa et al. Jpn. Pharmacol. Ther. "Proton pump inhibitor in rats, mice and dogs" 18 (1990) 165–187 (transl.).

H. Katsuki et al. "Determination of R(+)–and S(–)–Lansoprazole" Pharmaceutical Research 13(4) (1996) 611–615.

M. Tanaka et al. "Direct determination of pantoprazole enantiomers . . . " Anal. Chem. 68 (1996) 1513–1516.

P. Lindberg et al. "Omeprazole: The first proton pump inhibitor" Medicinal Res. Rev. 10 (1990) 2–50.

P. Lindberg et al. "The mechanism of action of . . . omeprazole" Journal of Medicinal Chemistry 29 (1986) 1327.

A. Brandsrom "Chemical reactions . . . " Reprint from Acta Chemica Scandinavica 43 (1989) 536–611.

K. Sigrist–Nelson et al. "Ro 18–5364, a potent inhibitor of the gastric ($H^+ + K^+$)–ATPase" Eur. J. Bioch. 166 (1987) 453.

CA 117:90292, Palomo et al.

*Primary Examiner*—Jane Fan
*Attorney, Agent, or Firm*—White & Case LLP

[57] ABSTRACT

The novel optically pure compounds $Na^+$, $Mg^{2+}$, $Li^+$, $K^+$, $Ca^{2+}$ and $N^+(R)_4$ salts of (+)-5-methoxy-2-[[(4-methoxy-3,5-dimethyl-2-pyridinyl)methyl]sulfinyl]-1H-benzimidazole or (−)-5-methoxy-2-[[(4-methoxy-3,5-dimethyl-2-pyridinyl)methyl]sulfinyl]-1H-benzimidazole, in particular sodium and magnesium salt form thereof, where R is an alkyl with 1–4 carbon atoms, processes for the preparation thereof and pharmaceutical preparations containing the compounds as active ingredients, as well as the use of the compounds in pharmaceutical preparations and intermediates obtained by preparing the compounds.

12 Claims, No Drawings

COMPOUNDS

This application is a continuation of application Ser. No. 08/899,931, filed on Jul. 24, 1997, now abandoned which is a continuation application of Ser. No. 08/376,512, filed Jan. 23, 1995; now U.S. Pat. No. 5,714,504 which is a continuation-in-part of Ser. No. 08/256,174, filed Jun. 28, 1994 now U.S. Pat. No. 5,693,818.

FIELD OF THE INVENTION

The present invention is directed to new compounds of high optical purity and crystalline salts thereof, their use in medicine, a process for their preparation and their use in the manufacture of pharmaceutical preparation. The invention also relates to novel intermediates in the preparation of the compounds of the invention.

BACKGROUND OF THE INVENTION

The compound 5-methoxy-2-[[(4-methoxy-3,5-dimethyl-2-pyridinyl)methyl]sulfinyl]-1H-benzimidazole, having the generic name omeprazole, and therapeutically acceptable alkaline salts thereof are described in U.S. Pat. No. 4,255,431 to Junggren et al., EP 5129 and EP 124 495, respectively. Omeprazole and its alkaline salts are effective gastric acid secretion inhibitors, and are useful as antiulcer agents. The compounds, being sulfoxides, have an asymmetric center in the sulfur atom, i.e. exist as two optical isomers (enantiomers).

The separation of the enantiomers of omeprazole in analytical scale is described in e.g. J. Chromatography, 532 (1990), 305–19 and in a preparative scale in DE 4035455. The latter has been done by using a diastereomeric ether which is separated and thereafter hydrolysed in an acidic solution. Under the acidic conditions needed for hydrolysis of the attached group, omeprazole is quite sensitive and the acid has to be quickly neutralized with a base to avoid degradation of the acid-sensitive compound. In the above mentioned application (DE 4035455) this is done by adding the reaction mixture containing concentrated sulfuric acid to a concentrated solution of NaOH. This is disadvantageous because there is a great risk of locally reaching pH values between 1–6, which would be devastating for the substance. Moreover, instantaneous neutralization will create heat which will be difficult to handle in large scale production.

There is no example in the known prior art of any isolated or characterized salt of optically pure omeprazole, i.e. of single enantiomers of omeprazole or of any isolated or characterized salt of any optically pure omeprazole analogue.

SUMMARY OF THE INVENTION

It is desirable to obtain compounds with improved pharmacokinetic and metabolic properties which will give an improved therapeutic profile such as a lower degree of interindividual variation. The present invention provides such compounds, which are novel salts of single enantiomers of omeprazole.

A preferred embodiment of the present invention provides pure crystalline enantiomeric salts of omeprazole and methods for the preparation thereof.

A more preferred embodiment of the present invention is directed to an optically pure crystalline enantiomeric magnesium salt of omeprazole and method for the preparation thereof.

A nonaqueous process according to the present invention is directed to the preparation of crystalline forms of an optically pure enantiomer of omeprazole magnesium salt or analogues thereof which includes steps of stirring a crude preparation of the omeprazole enantiomer under nitrogen into a methanolic magnesium methoxide solution, precipitating inorganic magnesium salt with addition of a small amount of water, removing any precipitated inorganic magnesium salts, concentrating the residual methanolic solution, precipitating the omeprazole enantiomer by adding acetone to the residual solution, and filtering off the optically pure enantiomer crystals of magnesium omeprazole or analogues thereof.

The present invention in a further aspect provides a novel method for preparing the novel compounds of the invention in large scale. This novel method can also be used in large scale to obtain single enantiomers of omeprazole in neutral form.

The compounds according to the invention may be used for inhibiting gastric acid secretion in mammals and man. In a more general sense, the compounds of the invention may be used for the treatment of gastric acid-related diseases and gastrointestinal inflammatory diseases in mammals and man, such as gastric ulcer, duodenal ulcer, reflux esophagitis, and gastritis. Furthermore, the compounds may be used for treatment of other gastrointestinal disorders where gastric antisecretory effect is desirable e.g. in patients on NSAID therapy, in patients with gastrinomas, and in patients with acute upper gastrointestinal bleeding. They may also be used in patients in intensive care situations, and pre- and postoperatively to prevent acid aspiration and stress ulceration. The compound of the invention may also be used for treatment or prophylaxis of inflammatory conditions in mammals, including man, especially those involving lysozymal enzymes. Conditions that may be specifically mentioned for treatment are rheumatoid arthritis and gout. The compound of the invention may also be useful in the treatment of psoriasis as well as in the treatment of Helicobacter infections.

DETAILED DESCRIPTION OF THE INVENTION

The present invention refers to the new $Na^+$, $Mg^{2+}$, $Li^+$, $K^+$, $Ca^{2+}$ and $N^+(R)_4$ salts of the single enantiomers of omeprazole, where R is an alkyl with 1–4 carbon atoms, i.e. $Na^+$, $Mg^{2+}$, $Li^+$, $K^+$, $Ca^{2+}$ and $N^+(R)_4$ salts of (+)-5-methoxy-2-[[(4-methoxy-3,5-dimethyl-2-pyridinyl)methyl]sulfinyl]-1H-benzimidazole and (−)-5-methoxy-2-[[(4-methoxy-3,5-dimethyl-2-pyridinyl)methyl]sulfinyl]-1H-benzimidazole, where R is an alkyl with 1–4 carbon atoms.

Particularly preferred salts according to the invention are the $Na^+$, $Ca^{2+}$ and $Mg^{2+}$ salts, i.e (+)-5-methoxy-2-[[(4-methoxy-3,5-dimethyl-2-pyridinyl)methyl]sulfinyl]1H-benzimidazole sodium salt, (−)-5-methoxy-2-[[(4-methoxy-3,5-dimethyl-2-pyridinyl)methyl]sulfinyl]-1H-benzimidazole sodium salt, (+)-5-methoxy-2-[[(4-methoxy-3,5-dimethyl-2-pyridinyl)methyl]sulfinyl]-1H-benzimidazole magnesium salt, (−)-5-methoxy-2-[[(4-methoxy-3,5-dimethyl-2-pyridinyl)methyl]sulfinyl]-1H-benzimidazole magnesium salt, (+)-5-methoxy-2-[[(4-methoxy-3,5-dimethyl-2-pyridinyl)methyl]sulfinyl]-1H-benzimidazole calcium salt and (−)-5-methoxy-2-[[(4-methoxy-3,5-dimethyl-2-pyridinyl)methyl]sulfinyl]-1H-benzimidazole calcium salt.

Most preferred salts according to the invention are the optically pure $Na^+$ salts of omeprazole according to compounds Ia and Ib (Ia, Ib)

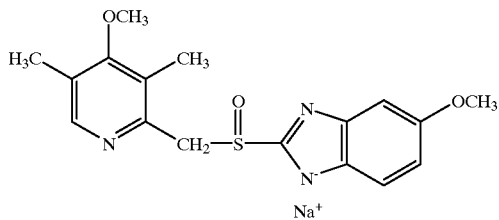

Ia (+)-enantiomer
Ib (−)-enantiomer and the optically pure magnesium salts of omeprazole according to compounds IIa and IIb (IIa, IIb)

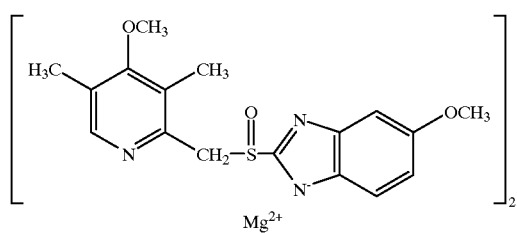

IIa (+)-enantiomer
IIb (−)-enantiomer

With the expression "optically pure Na$^+$ salts of omeprazole" is meant the (+)-enantiomer of omeprazole Na-salt essentially free of the (−)-enantiomer of omeprazole Na-salt and the (−)-enantiomer essentially free of the (+)-enantiomer, respectively. Single enantiomers of omeprazole have hitherto only been obtained as syrups and not as crystalline products. The salts defined by the present invention are easy to obtain by means of the novel specific method according to one aspect of the invention of preparing the single enantiomers of omeprazole. In contrast to the neutral forms the salts can be obtained as crystalline products. Because it is possible to purify optically impure or partially pure salts of the enantiomers of omeprazole by crystallization, they can be obtained in very high optical purity, namely ≧99.8% enantiomeric excess (e.e.) even from an optically contaminated preparation. Moreover, the optically pure salts are stable resisting racemization both in neutral pH and basic pH, which is surprising since the known deprotonation at the carbon atom between the pyridine ring and the chiral sulfur atom was expected to cause racemization under alkaline conditions. This high stability against racemization makes it possible to use a single enantiomeric salt of the invention in therapy.

The specific method of preparation of the single enantiomers of omeprazole is a further aspect of the invention as mentioned above and it can be used to obtain the single enantiomers of omeprazole in neutral form as well as the salts thereof.

Yet a further aspect of the invention is the compound III, which is an intermediate used in the specific method of preparation.

(III)

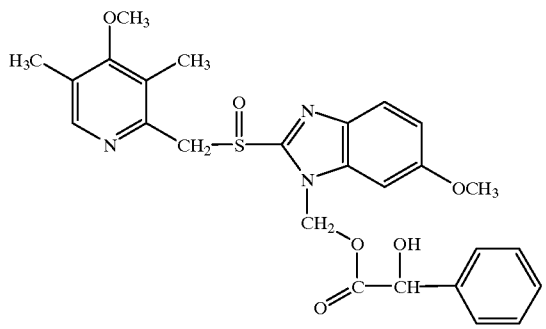

Preparation

The optically pure compounds of the invention, i.e. the single enantiomers, are prepared by separating the two stereoisomers of a diastereomeric mixture of the following type, 5- or 6-methoxy-2-[[(4-methoxy-3,5-dimethyl-2-pyridinyl)methyl]sulfinyl]-1-[acyloxymethyl]-1H-benzimidazole, formula IV (IV)

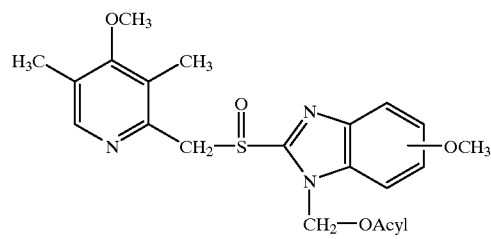

wherein the methoxy substituent in the benzimidazole moiety is in position 5 or 6, and wherein the Acyl radical is as defined below, followed by a solvolysis of each separated diastereomer in an alkaline solution. The formed single enantiomers of omeprazole are then isolated by neutralizing aqueous solutions of the salts of the single enantiomers of omeprazole with a neutralizing agent which can be an acid or an ester such as methyl formate.

The Acyl moiety in the diastereomeric ester may be a chiral acyl group such as mandeloyl, and the asymmetric center in the chiral acyl group can have either R or S configuration.

The diastereomeric esters can be separated either by chromatography or fractional crystallization.

The solvolysis usually takes place together with a base in a protic solvent such as alcohols or water, but the acyl group may also be hydrolyzed off by a base in an aprotic solvent such as dimethylsulfoxide or dimethylformamide. The reacting base may be OH$^-$ or R$^1$O$^-$ where R$^1$ can be any alkyl or aryl group.

To obtain the optically pure Na$^+$ salts of the invention, i.e. the single enantiomers of omeprazole Na$^+$ salts, the resulting compound is treated with a base, such as NaOH, in an aqueous or nonaqueous medium, or with NaOR$^2$ wherein R$^2$ is an alkyl group containing 1–4 carbon atoms, or with NaNH$_2$. In addition, alkaline salts wherein the cation is Li$^+$ or K$^+$ may be prepared using lithium or potassium salts of the above mentioned bases. In order to obtain the crystalline form of the Na$^+$ salt, addition of NaOH in a non-aqueous medium such as a mixture of 2-butanone and toluene, is preferred.

To obtain the optically pure $Mg^{2+}$ salts of the invention, optically pure enantiomeric $Na^+$ salts may be treated with an aqueous solution of an inorganic magnesium salt such as $MgCl_2$, whereupon the $Mg^{2+}$ salts are precipitated. The optically pure $Mg^{2+}$ salts may also be prepared by treating single enantiomers of omeprazole with a base, such as $Mg(OR^3)_2$, wherein $R^3$ is an alkyl group containing 1–4 carbon atoms, in a non-aqueous solvent such as alcohol (only for alcoholates), e.g. ROH, or in an ether such as tetrahydrofuran. In an analogous way, also alkaline salts wherein the cation is $Ca^{2+}$ can be prepared, using an aqueous solution of an inorganic calcium salt such as $CaCl_2$.

Alkaline salts of the single enantiomers of the invention are, as mentioned above, beside the sodium salts (compounds Ia and Ib) and the magnesium salts (compounds Ia and IIb), exemplified by their salts with $Li^+$, $K^+$, $Ca^{2+}$ and $N^+(R)_4$, where R is an alkyl with 1–4 C-atoms.

For clinical use the single enantiomers, i.e. the optically pure compounds, of the invention are formulated into pharmaceutical formulations for oral, rectal, parenteral or other modes of administrations. The pharmaceutical formulations contain the single enantiomers of the invention normally in combination with a pharmaceutically acceptable carrier. The carrier may be in form of a solid, semisolid or liquid diluent, or capsule. These pharmaceutical preparations are a further object of the invention. Usually the amount of active compound is between 0.1–95% by weight of the preparation, between 0.2–20% by weight in preparations for parenteral use and between 1–50% by weight in preparations for oral administration.

In the preparation of pharmaceutical formulations in form of dosage units for oral administration the optically pure compound may be mixed with a solid, powdered carrier, such as lactose, saccharose, sorbitol, mannitol, starch, amylopectin, cellulose derivates, gelatin or another suitable carrier, stabilizing substances such as alkaline compounds e.g. carbonates, hydroxides and oxides of sodium, potassium, calcium, magnesium and the like as well as with lubricating agents such as magnesium stearate, calcium stearate, sodium stearyl fumarate and polyethyleneglycol waxes. The mixture is then processed into granules or pressed into tablets. Granules and tablets may be coated with an enteric coating which protects the active compound from acid catalyzed degradation as long as the dosage form remains in the stomach. The enteric coating is chosen among pharmaceutically acceptable enteric-coating materials e.g. beeswax, shellac or anionic film-forming polymers and the like, if preferred in combination with a suitable plasticizer. To the coating various dyes may be added in order to distinguish among tablets or granules with different amounts of the active compound present.

Soft gelatine capsules may be prepared with capsules containing a mixture of the active compound, vegetable oil, fat, or other suitable vehicle for soft gelatine capsules. Soft gelatine capsules may also be enteric-coated as described above.

Hard gelatine capsules may contain granules or enteric-coated granules of the active compound. Hard gelatine capsules may also contain the active compound in combination with a solid powdered carrier such as lactose, saccharose, sorbitol, mannitol, potato starch, amylopectin, cellulose derivates or gelatin. The capsules may be enteric-coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparation for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and/or polyethylene glycol. If desired, such liquid preparations may contain coloring agents, flavoring agents, saccharine and carboxymethyl cellulose or other thickening agents. Liquid preparations for oral administration may also be prepared in the form of dry powder to be reconstituted with a suitable solvent prior to use.

Solutions for parenteral administrations may be prepared as solutions of the optically pure compounds of the invention in pharmaceutically acceptable solvents, preferably in a concentration from 0.1 to 10% by weight. These soultions may also contain stabilizing agents and/or buffering agents and may be manufactured in different unit dose ampoules or vials. Solutions for parenteral administration may also be prepared as dry preparations to be reconstituted with a suitable solvent extemporaneously before use.

The typical daily dose of the active compound will depend on various factors such as for example the individual requirement of each patient, the route of administration and the disease. In general, oral and parenteral dosages will be in the range of 5 to 500 mg per day of active substance.

The invention is illustrated by the following examples using preferred procedures for the preparation of optically pure sodium salts and magnesium salts.

The processes described below for optically pure enantiomeric sodium salts of omeprazole result in change of directions from (−) to (+) optical rotation and, vice versa, from (+) to (−) optical rotation when preparing the sodium salt from the neutral form of omeprazole and again, when preparing the magnesium salt from the sodium salt of omeprazole.

EXAMPLE 1

Preparation of (+)-5-methoxy-2-[[(4-methoxy-3,5-dimethyl-2-pyridinyl)methyl]sulfinyl]-1H-benzimidazole sodium salt 100 mg (0.3 mmol) of (−)-5-methoxy-2-[[(4-methoxy-3,5-dimethyl-2-pyridinyl)-methyl]sulfinyl]-1H-benzimidazole (contaminated with 3% of the (+)-isomer) was dissolved in 1 ml of 2-butanone with stirring. 60 μl of an aqueous solution of 5.0 M sodium hydroxide and 2 ml of toluene were added. The resultant mixture was non-homogeneous. In order to obtain a clear solution, more 2-butanone was added (ca 1 ml) and the mixture was stirred at ambient temperature over night. The formed precipitate was filtered off and washed with ether. There was obtained 51 mg (46%) of the title compound as white crystals m.p. (decomposition) 246–248° C. The optical purity (e.e.) which was analyzed by chiral column chromatography was ≧99.8%. $[\alpha]_D^{20}$=+42,8° (concentration, c=0.5%, water).

NMR data are given below.

EXAMPLE 2

Preparation of (−)-5-methoxy-2-[[(4-methoxy-3,5-dimethyl-2-pyridinyl)methyl]sulfinyl]-1H-benzimidazole sodium salt 100 mg-(0.3 mmol)of(+)-5-methoxy-2-[[(4-methoxy-3,5-dimethyl-2-pyridinyl)-methyl]sulfinyl]-1H-benzimidazole (contaminated with 3% of the (−)-isomer) was dissolved in 1 ml of 2-butanone with stirring. 60 μl of an aqueous solution of 5.0 M sodium hydroxide and 2 ml of toluene were added. The resultant mixture was non-homogeneous. In order to obtain a clear solution, more 2-butanone was added (ca 1 ml) and the mixture was stirred at ambient temperature over night. The formed precipitate was filtered off and washed with ether. There was obtained 56 mg (51%) of the title compound as white crystals m.p. (decomposition) 247–249° C. The optical purity (e.e.) which was analyzed by chiral column chromatography was ≧99.8%. $[\alpha]_D^{20}=-44.1°$ (c=0.5%, water).

NMR data are given below.

EXAMPLE 3

Preparation of (+)-5-methoxy-2-[[(4-methoxy-3,5-dimethyl-2-pyridinyl)methyl]sulfinyl]-1H-benzimidazole magnesium salt 2.9 ml of a 0.1 M solution of NaOH was added to 0.10 g (0.29 mmol) (+)-5-methoxy-2-[[(4-methoxy-3,5-dimethyl-2-pyridinyl)methyl]sulfinyl]-1H-benzimidazole. To this mixture 2 ml methylene chloride was added, and after mixing in a separatory funnel the aqueous solution was separated off. A solution of 14 mg (0.145 mmol) $MgCl_2$ in water was added dropwise. The formed precipitate was isolated by centrifugation, and 52 mg (50%) of the product was isolated as an amorphous powder. The optical purity (e.e.) was 98%, and thus the same as the starting material. The optical purity was determined by chromatography on an analytical chiral column. $[\alpha]_D^{20}=+101.2°$ (c=1%, methanol). The Mg content of the sample was found to be 3.0%, shown by atomic absorption spectroscopy.

EXAMPLE 4

Preparation of (+)-5-methoxy-2-[[(4-methoxy-3,5-dimethyl-2-pyridinyl)methyl]sulfiinyl]-1H-benzimidazole magnesium salt (−)-5-methoxy-2-[[(4-methoxy-3,5-dimethyl-2-pyridinyl)methyl]sulfinyl]-1H-benzimidazole sodium salt (0.500 g, 1.36 mmol) was dissolved in water (10 ml). To this mixture 10 ml of an aqueous solution of $MgCl_2 \times H_2O$ (138 mg, 0.68 mmol) was added dropwise and the formed precipitate was isolated by centrifugation. There was obtained 418 mg (86%) of the product as a white powder. The optical purity (ee) of the product was 99.8% which was the same as the optical purity of the starting material. The optical purity was determined by chromatography on an analytical chiral column. $[\alpha]_D^{20}=+129.9°$ (c=1%, methanol).

EXAMPLE 5

Preparation of (−)-5-methoxy-2-[[(4-methoxy-3,5-dimethyl-2-pyridinyl)methyl]sulfinyl]-1H-benzimidazole magnesium salt (+)-5-methoxy-2-[[(4-methoxy-3,5-dimethyl-2-pyridinyl)methyl]-sulfinyl]-1H-benzimidazole sodium salt (0.165 g, 0.45 mmol) was dissolved in water (3 ml). To this mixture 2 ml of an aqueous solution of $MgCl_2 \times H_2O$ (46 mg, 0.23 mmol) was added dropwise and the formed precipitate was isolated by centrifugation. There was obtained 85 mg (51%) of the product as a white powder. The optical purity (ee) of the product was 99.9% which was the same or better as the optical purity of the starting material. The optical purity was determined by chromatography on an analytical chiral column. $[\alpha]_D^{20}=-128.2°$ (c=1%, methanol).

TABLE 1

| Ex. | Solvent | NMR data δ ppm |
|---|---|---|
| 1. | DMSO-$d_6$ 500 MHz | 2.20 (s, 3H), 2.22 (s, 3H), 3.69 (s, 3H), 3.72 (s, 3H), 4.37 (d, 1H), 4.75 (d, 1H), 6.54 (dd, 1H), 6.96 (d, 1H), 7.30 (d, 1H), 8.21 (s, 1H). |
| 2. | DMSO-$d_6$ 500 MHz | 2.20 (s, 3H), 2.22 (s, 3H), 3.69 (s, 3H), 3.72 (s, 3H), 4.38 (d, 1H), 4.73 (d, 1H), 6.54 (dd, 1H), 6.96 (d, 1H), 7.31 (d, 1H), 8.21 (s, 1H). |

A preferred method for preparing optically pure omeprazole enantiomer crystal salts of magnesium is described in Examples 6 and 7.

EXAMPLE 6

Enhancement of the optical purity by preparing the magnesium salt of (−)-5-methoxy-2-[[4-methoxy-3,5-dimethyl-2-pyridinyl)-methyl]sulfinyl]-1H-benzimidazole in nonagueous solution followed by crystallization of said salt Magnesium (0.11 g, 4.5 mmol) was dissolved and reacted with methanol (50 ml) at 40° C. with a catalytic amount of methylene chloride. The reaction was run under nitrogen and was finished after five hours. At room temperature a mixture of the two enantiomers [90%(−)-isomer and 10%(+)-isomer] of 5-methoxy-2-[[4-methoxy-3,5-dimethyl-2-pyridinyl)methyl]sulfinyl]-1H-benzimidazole (2.84 g, 8.2 mmol) was added to the magnesium methoxide solution. The mixture was stirred for 12 hours whereupon a small amount of water (0.1 ml) was added in order to precipitate inorganic magnesium salts. After 30 minutes stirring, these inorganic salts were filtered off and the solution was concentrated on a rotavapor. The residue was now a concentrated methanolic solution of the enantiomeric mixture (i.e. the title compound contaminated with the (+)-isomer), with an optical purity (enantiomeric excess, e.e.) of 80%. This mixture was diluted with acetone (100 ml) and after stirring at room temperature for 15 minutes, a white precipitate was obtained. Additional stirring for 15 mintues and thereafter filtration afforded 1.3 g (50%) of the title compound as white crystals. Chiral analyses of the crystals and mother liquor were performed by chromatography on an analytical chiral column. The optical purity of the crystals and mother liquor was found to be 98.4 e.e. and 64.4% e.e., respectively. Thus, the optical purity (e.e.) has been enhanced from 80% to 98.4% simply by crystallizing the Mg-salt from a mixture of acetone and methanol. The product was crystalline as shown by powder X-ray diffraction and the magnesium content was 3.44% as shown by atomic absorption spectroscopy. $[\alpha]_D^2=-131.5°$ (c=0.5%, methanol).

EXAMPLE 7

Enhancement of the optical purity by preparing the magnesium salt of (+)-5-methoxy-2-[[4-methoxy-3,5-dimethyl-2-pyridinyl)-methyl]sulfinyl]-1H-benzimidazole in nonaqueous solution followed by crystallization of said salt Magnesium (0.11 g, 4.5 mmol) was dissolved and reacted with methanol (50 ml) at 40° C. with a catalytic amount of methylene chloride. The reaction was run under nitrogen and was finished after five hours. At room temperature a mixture of the two enantiomers [90%(+)-isomer and 10%(−)-isomer]

of 5-methoxy-2-[[4-methoxy-3,5-dimethyl-2-pyridinyl) methyl]sulfinyl]-1H-benzimidazole (2.84 g, 8.2 mmol) was added to the magnesium methoxide solution. The mixture was stirred for 12 hours whereupon a small amount of water (0.1 ml) was added in order to precipitate inorganic magnesium salts. After 30 minutes stirring, these inorganic salts were filtered off and the solution was concentrated on a rotavapor. The residue was now a concentrated methanolic solution of the enantiomeric mixture (i.e. the title compound contaminated with the (−)-isomer), with an optical purity (e.e.) of 80%. This mixture was diluted with acetone (100 ml) and after stirring at room temperature for one hour, a white precipitate was obtained. Additonal stirring for 30 minutes and thereafter filtration afforded 0.35 g of the title compound as white crystals. Additional stirring of the mother liquor for 24 hours at room temperature afforded another 1.0 g (total yield=52%). Chiral analyses of the crystals and the second mother liquor were performed by chromatography on an analytical chiral column. The optical purity of the two crystal fractions was 98.8% e.e. and 99.5% e.e., respectively. The optical purity of the mother liquor was found to be 57% e.e. Thus, the optical purity (e.e.) has been enhanced from 80% to approximately 99% simply by crystallizing the Mg-salt from a mixture of acetone and methanol. The first precipitation was crystalline as shown by powder X-ray diffraction and the magnesium content of the same fraction was 3.49% as shown by atomic absorption spectroscopy. $[\alpha]_D^{20}=+135.6°$ (c=0.5%, methanol).

The crystalline salt according to Example 6 is most preferred.

Preparation of the synthetic intermediates according to the invention is described in the following examples.

EXAMPLE 8

Preparation of 6-methoxy-2-[[(4-methoxy-3,5-dimethyl-2-pyridinyl)methyl]-(R/S)-sulfinyl]-1-[(R)-mandeloyloxymethyl]-1H-benzimidazole A solution of 3.4 g sodium hydroxide in 40 ml water was added to a mixture of 14.4 g (42 mmol) tetrabutylammonium hydrogen sulfate and 6.4 g (42 mmol) (R)(−)-mandelic acid. The mixture was extracted with 400 ml chloroform. After separation, the organic extract was heated to reflux with 16.6 g (42 mmol) of the racemate of 6-methoxy-2-[[(4-methoxy-3,5-dimethyl-2-pyridinyl)methyl]-sulfinyl]-1-[chloromethyl]-1H-benzimidazole. Evaporation of the solvent was followed by dilution with 100 ml dichloromethane and 700 ml ethyl acetate. The mixture was washed with 3×200 ml water and the organic solution was dried over MgSO$_4$ and then evaporated. The crude material was purified by recrystallization from 100 ml acetonitrile, giving 8.1 g of the title compound (38%) as a diastereomeric mixture.

NMR data are given below.

EXAMPLE 9

Separation of the more hydrophilic diastereomer of 6-methoxy-2-[[(4-methoxy-3,5-dimethyl-2-pyridinyl)methyl]-(R/S)-sulfinyl]-1[(R) mandeloyloxymethyl]-1H-benzimidazole The diastereomers of the title compound in Example 8 were separated using reversed phase chromatography (HPLC). Approximately 300 mg of the diastereomeric mixture was dissolved in 10 ml hot acetonitrile which was diluted with 10 ml of a mixture of aqueous 0.1 M ammoniumacetate and acetonitrile (70/30). The solution was injected to the column and the compounds were eluted with a mixture of aqueous 0.1 M ammoniumacetate and acetonitrile (70/30). The more hydrophilic isomer was easier to obtain pure than the less hydrophilic one. The work up procedure for the fraction which contained pure isomer was as follows; extraction with dichloromethane, washing the organic solution with aqueous 5% sodium hydrogen carbonate solution, drying over Na$_2$SO$_4$ and evaporation of the solvent on a rotavapor (at the end of the evaporation the removal of acetonitrile was facilitated by adding more dichloromethane). Using 1.2 g of the diastereomeric mixture with the above mentioned technique, the more hydrophilic isomer, 410 mg, was obtained in a pure state as a colorless syrup.

NMR data are given below.

EXAMPLE 10

Preparation of 6-methoxy-2-[[(4-methoxy-3,5-dimethyl-2-pyridinyl)methyl]-(R/S)-sulfinyl]-1-[(S)-mandeloyloxymethyl]-1H-benzimidazole The product was obtained from 8.1 g (202 mmol) sodium hydroxide in 100 ml water, 34.4 g (101 mmol) tetrabutylammonium hydrogen sulfate, 15.4 g (101 mmol) (S)-(+)-mandelic acid and 39.9 g (101 mmol) of the racemate of 6-methoxy-2-[[(4-methoxy-3,5-dimethyl-2-pyridinyl) methyl]-sulfinyl]-1 -[chloromethyl]-1H-benzimidazole using the same procedure as in Example 8. Recrystallization from 100 ml acetonitrile yielded 21.3 g, i.e. 41% of the title compound as a diastereomeric mixture.

NMR data are given below.

EXAMPLE 11

Separation of the more hydrophilic diastereomer of 6-methoxy-2-[[(4-methoxy-3,5-dimethyl-2-pyridinyl)methyl]-(R/S)-sulfinyl]-1-[(S)-mandeloyloxymethyl]-1H-benzimidazole The diastereomers of the title compound in Example 10 were separated using reversed phase chromatography (HPLC) in the same way as in Example 7, but using the diasteromeric mixture of 6-methoxy-2-[[(4-methoxy-3,5-dimethyl-2-pyridinyl)methyl]-(R/S)-sulfinyl]-1-[(S)-mandeloloxymethyl]-1H-benzimidazole instead of the (R)-mandelic ester used in Example 9. Using 2.1 g of the diastereomeric mixture, the more hydrophilic isomer, 760 mg, was obtained in a pure state as a colorless syrup.

NMR data are given below.

EXAMPLE 12

Preparation of (−)-5-methoxy-2-[[(4-methoxy-3,5-dimethyl-2-pyridinyl)methyl]-sulfinyl]-1H-benzimidazole 0.23 g (0.45 mmol) of the more hydrophilic diastereomer of 6-methoxy-2-[[(4-methoxy-3,5-dimethyl-2-pyridinyl) methyl]sulfinyl]-1-[(R)-mandeloyloxymethyl]-1H-benzimidazole was dissolved in 15 ml methanol. A solution of 36 mg (0.9 mmol) sodium hydroxide in 0.45 ml water was added, and after 10 minutes the mixture was evaporated on a rotavapor. The residue was partitioned between 15 ml water and 15 ml dichloromethane. The organic solution was extracted with 15 ml water and to the combined aqueous solutions was added 85 μl (1.4 mmol) methyl formate. After 15 minutes the mixture was extracted with 3×10 ml dichloromethane. The organic solution was dried over Na$_2$SO$_4$ and then evaporated. There was obtained 0.12 g (77%) of the title compound as a colorless syrup. The optical purity (e.e.) which was analyzed by chiral column chromatography was 94%. $[\alpha]_D^{20}=-155°$ (c=0.5%, chloroform).

NMR data are given below

EXAMPLE 13

Preparation of (+)-5-methoxy-2-[[(4-methoxy-3,5-dimethyl-2-pyridinyl)methyl]-sulfinyl]-1H-benzimidazole 0.76 g (1.5 mmol) of the more hydrophilic diastereomer of 6-methoxy-2-[[(4-methoxy-3,5-dimethyl-2-pyridinyl)methyl]sulfinyl]-1-[(S)-mandeloyloxymethyl]-1H-benzimidazole was dissolved in 50 ml methanol. A solution of 0.12 mg (3.0 mmol) sodium hydroxide in 1.5 ml water was added, and after 10 minutes the mixture was evaporated on a rotavapor. The residue was partitioned between 25 ml water and 25 ml dichloromethane. The organic solution was extracted with 25 ml water and to the combined aqueous solutions was added 200 µl (3.2 mmol) methyl formate. After 15 minutes the mixture was extracted with 3×25 ml dichloromethane. The organic solution was dried over $Na_2SO_4$ and then evaporated. There was obtained 0.42 g (81%) of the title compound as a colorless syrup. The optical purity (e.e.) which was analyzed by chiral column chromatography was 98%. $[\alpha]_D^{20}=+157°$ (c=0.5%, chloroform).

NMR data are given below

TABLE 2

| Ex. | Solvent | NMR data δ ppm |
|---|---|---|
| 8. | CDCl$_3$ 500 MHz | 2.18 (s, 3H), 2.20 (s, 3H), 2.36 (s, 3H), 2.39 (s, 3H), 3.77 (s, 3H), 3.78 (s, 3H), 3.82 (s, 3H), 3.87 (s, 3H), 4.80 (d, m), 4.88 (d, 1H), 5.0 (m, 2H), 5.34 (s, 2H), 6.43 (d, 1H), 6.54 (d, 1H), 6.6–6.7 (m, 2H), 6.96 (d, 1H), 6.95–6.98 (m, 2H), 7.01 (d, 1H), 7.2–7.3 (m, 6H), 7.37 (m, 2H), 7.44 (m, 2H), 7.58 (d, 1H), 7.62 (d, 1H), 7.95 (s, 1H), 7.97 (s, 1H). |
| 9. | CDCl$_3$ 500 MHz | 2.20 (s, 3H), 2.36 (s, 3H), 3.78 (s, 3H), 3.82 (s, 3H), 4.80 (d, 1H), 5.00 (d, 1H), 5.35 (d, 1H), 6.43 (d, 1H), 6.63 (d, 1H), 6.90 (d, 1H), 6.97 (dd, 1H), 7.2–7.3 (m, 3H), 7.37 (m, 2H), 7.62 (d, 1H), 7.97 (s, 1H). |
| 10. | CDCl$_3$ 500 MHz | 2.19 (s, 3H), 2.20 (s, 3H), 2.36 (s, 3H), 2.39 (s, 3H), 3.77 (s, 3H), 3.78 (s, 3H), 3.83 (s, 3H), 3.87 (s, 3H), 4.80 (d, 1H), 4.88 (d, 1H), 5.0 (m, 2H), 5.34 (s, 2H), 6.43 (d, 1H), 6.54 (d, 1H), 6.6–6.7 (m, 2H), 6.90 (d, 1H), 6.96–6.98 (m, 2H), 7.01 (d, 1H), 7.2–7.3 (m, 6H), 7.37 (m, 2H), 7.44 (m, 2H), 7.58 (d, 1H), 7.62 (d, 1H), 7.95 (s, 1H), 7.97 (s, 1H). |
| 11. | CDCl$_3$ 500 MHz | 2.20 (s, 3H), 2.36 (s, 3H), 3.78 (s, 3H), 3.82 (s, 3H), 4.80 (d, 1H), 5.00 (d, 1H), 5.35 (d, 1H), 6.43 (d, 1H), 6.63 (d, 1H), 6.90 (d, 1H), 6.97 (dd, 1H), 7.2–7.3 (m, 3H), 7.37 (m, 2H), 7.62 (d, 1H), 7.97 (s, 1H). |
| 12. | CDCl$_3$ 300 MHz | 2.18, (s, 3H), 2.22 (s, 3H), 3.68 (s, 3H), 3.83 (s, 3H), 4.77(m, 2H), 6.93 (dd, 1H), ≈7.0 (1), 1H), ≈7.5 (b, 1H), 8.19 (s, 1H). |
| 13. | CDCl$_3$ | 2.21 (s, 3H), 2.23 (s, 3H), 3.69 (s, 3H), 3.84 (s, 3H), 4.76 (m, 2H), 6.94 (dd, 1H), 7.0 (1,, 1H), ≈7.5 (1), 1H), 8.20 (s, 1H). |

Pharmaceutical preparations containing the compounds of the invention as active ingredient are illustrated in the following formulations.

Syrup

A syrup containing 1% (weight per volume) of active substance was prepared from the following ingredients:

| Compound according to Example 1 | 1.0 g |
|---|---|
| Sugar, powder | 30.0 g |
| Saccharine | 0.6 g |
| Glycerol | 5.0 g |
| Flavoring agent | 0.05 g |
| Ethanol 96% | 5.0 g |
| Distilled water q.s. to a final volume of | 100 ml |

Sugar and saccharine were dissolved in 60 g of warm water. After cooling the active compound was added to the sugar solution and glycerol and a solution of flavoring agents dissolved in ethanol were added. The mixture was diluted with water to a final volume of 100 ml.

Enteric-coated tablets

An enteric coated tablet containing 50 mg of active compound was prepared from the following ingredients:

| I | Compound according to Example 6 as Mg salt | 500 g |
|---|---|---|
| | Lactose | 700 g |
| | Methyl cellulose | 6 g |
| | Polyvinylpyrrolidone cross-linked | 50 g |
| | Magnesium stearate | 15 g |
| | Sodium carbonate | 6 g |
| | Distilled water | q.s. |
| II | Cellulose acetate phthalate | 200 g |
| | Cetyl alcohol | 15 g |
| | Isopropanol | 2000 g |
| | Methylene chloride | 2000 g |

I Compound according to Example 6, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 50 mg of active substance, in a tabletting machine using 7 mm diameter punches.

II A solution of cellulose acetate phthalate and cetyl alcohol in isopropanol/methylene chloride was sprayed onto the tablets I in an Accela Cota$^R$, Manesty coating equipment. A final tablet weight of 110 mg was obtained.

Solution for intravenous administration

A parenteral formulation for intravenous use, containing 4 mg of active compound per ml, was prepared from the following ingredients:

| | |
|---|---|
| Compound according to Example 2 | 4 g |
| Sterile water to a final volume of | 1000 ml |

The active compound was dissolved in water to a final volume of 1000 ml. The solution was filtered through a 0.22 μm filter and immediately dispensed into 10 ml sterile ampoules. The ampoules were sealed.

Capsules

Capsules containing 30 mg of active compound were prepared from the following ingredients:

| | |
|---|---|
| Compound according to Example 6 | 300 g |
| Lactose | 700 g |
| Microcrystalline cellulose | 40 g |
| Hydroxypropyl cellulose low-substituted | 62 g |
| Disodium hydrogen phosphate | 2 g |
| Purified water | q.s. |

The active compound was mixed with the dry ingredients and granulated with a solution of disodium hydrogen phosphate. The wet mass was forced through an extruder and spheronized and dried in a fluidized bed dryer.

500 g of the pellets above were first coated with a solution of hydroxypropyl methylcellulose, 30 g, in water, 750 g, using a fluidized bed coater. After drying, the pellets were coated with a second coating as given below:

Coating solution:

| | |
|---|---|
| Hydroxypropyl methylcellulose phthalate | 70 g |
| Cetyl alcohol | 4 g |
| Acetone | 200 g |
| Ethanol | 600 g |

The final coated pellets were filled into capsules.

Suppositories

Suppositories were prepared from the following ingredients using a welding procedure. Each suppository contained 40 mg of active compound.

| | |
|---|---|
| Compound according to Example 1 | 4 g |
| Witepsol H-15 | 180 g |

The active compound was homogenously mixed with Witepsol H-15 at a temperature of 41° C. The molten mass was volume filled into pre-fabricated suppository packages to a net weight of 1.84 g. After cooling the packages were heat sealed. Each suppository contained 40 mg of active compound.

Stability towards racemization at different pH values

The stability of the optically pure compounds of the invention against racemization has been measured at low concentrations in a refrigerator in aqueous buffer solutions at pH 8, 9.3, 10 and 11.2. The stereochemical stability was measured by comparing the optical purity for the (−)-isomer of 5-methoxy-2-[[(4-methoxy-3,5-dimethyl-2-pyridinyl)-methyl]sulfinyl]-1H-benzimidazole in buffer solution immediately after dissolving and after several days. The measurement was performed by chromatography on an analytical chiral column. The surprising high stereochemical stability in alkaline conditions for the compounds of invention is exemplified by the fact that no racemization for the test compound was obtained at pH 11.2 even after 21 days. At pH 8, 9.3 and 10, the chemical degradation of the compound is more apparent which makes the racemization measurement more difficult to perform, however at none of these pH values a detectable racemization was obtained after 16 days.

In another racemization experiment with the optically pure compounds of the invention, an aqueous phosphate buffer solution (pH=11) of the (+)-isomer of 5-methoxy-2-[[(4-methoxy-3,5-dimethyl-2-pyridinyl)methyl]sulfinyl]-1H benzimidazole sodium salt (c=10$^{-5}$M) was warmed for 26 hours at 37° C. without any racemization at all being observed.

What is claimed is:

1. A pharmaceutical formulation for parenteral administration comprising an optically pure solid state Na$^+$salt of the (−)-enantiomer of 5-methoxy-2[[(4-methoxy-3,5-dimethyl-2-pyridinyl)methyl]sulfinyl]-1H-benzimidazole as active ingredient, and a pharmaceutically acceptable carrier.

2. A pharmaceutical formulation for parenteral administration comprising an injection solution comprising an optically pure solid state Na$^+$ salt of the (−)-enantiomer of 5-methoxy-2[[(4-methoxy-3,5-dimethyl-2-pyridinyl) methyl]sulfinyl]-1H-benzimidazole as active ingredient, and a pharmaceutically acceptable carrier in the form of a pharmaceutically acceptable solvent having a volume sufficient to effect a solution having a concentration of 0.1 to 10% by weight of the active ingredient.

3. The pharmaceutical formulation according to claim 1 or 2, wherein the solid state salt is in substantially crystalline form.

4. The pharmaceutical formulation according to claim 1 or 2, further comprising a stabilizing agent, a buffering agent or a mixture thereof.

5. The pharmaceutical formulation for parenteral administration according to claim 1, comprising an injectable solution.

6. A method of inhibiting gastric acid secretion comprising the parenteral administration to a mammal including man in need of such treatment of a pharmaceutical formulation comprising a therapeutically effective amount of an optically pure solid state Na$^+$ salt of the (−)-enantiomer of 5-methoxy-2[[(4-methoxy-3,5-dimethyl-2-pyridinyl) methyl]sulfinyl]-1H-benzimidazole and a pharmaceutically acceptable carrier.

7. A method for the treatment of gastrointestinal inflammatory disease comprising the parenteral administration to a mammal including man in need of such treatment of a pharmaceutical formulation comprising a therapeutically effective amount of an optically pure solid state Na$^+$ salt of the (−)-enantiomer of 5-methoxy-2[[(4-methoxy-3,5-dimethyl-2-pyridinyl)methyl]sulfinyl]-1H-benzimidazole, and a pharmaceutically acceptable carrier.

8. The method according to claim 7, wherein a solution with the solvent carrier is prepared immediately before the administration.

9. The method according to claim 6 or 7, wherein the pharmaceutically acceptable carrier is in the form of a solvent.

10. The method of claim 7, wherein the solvent has a volume effecting a solution of a concentration of 0.1–10% by weight of the active ingredient.

11. A method of inhibiting gastric acid secretion comprising injecting a mammal including man in need of such treatment with a solution of an optically pure solid state $Na^+$ salt of the (−)-enantiomer of 5-methoxy-2[[(4-methoxy-3,5-dimethyl-2-pyridinyl)methyl]sulfinyl]-1H-benzimidazole and a pharmaceutically acceptable solvent having a volume sufficient to effect a solution having a concentration of 0.1 to 10% by weight of the active ingredient.

12. A method for the treatment of gastrointestinal inflammatory disease comprising injecting a mammal including man in need of such treatment with a solution of an optically pure solid state $Na^+$ salt of the (−)-enantiomer of 5-methoxy-2[[(4-methoxy-3,5-dimethyl-2-pyridinyl)methyl]sulfinyl]-1H-benzimidazole and a pharmaceutically acceptable solvent having a volume sufficient to effect a solution having a concentration of 0.1 to 10% by weight of the active ingredient.

* * * * *

UNITED STATES PATENT AND TRADEMARK OFFICE
CERTIFICATE OF CORRECTION

PATENT NO.  : 6,143,771
DATED       : November 7, 2000
INVENTOR(S) : Lindberg, et al.

It is certified that error appears in the above-identified patent and that said Letters Patent is hereby corrected as shown below:

In claim 8, col. 15, line 1, delete "claim 7" and substitute therefor -- claim 9 --.

In claim 10, col. 15, line 7, delete "claim 7" and substitute therefor -- claim 9 --.

Signed and Sealed this

Eighth Day of May, 2001

Attest:

NICHOLAS P. GODICI

*Attesting Officer*    Acting Director of the United States Patent and Trademark Office